(12) United States Patent
Camacho

(10) Patent No.: US 10,492,942 B2
(45) Date of Patent: Dec. 3, 2019

(54) PRESSURIZED TREATMENT DEVICES AND METHODS OF USE THEREOF

(71) Applicant: Alexander J. Camacho, Natick, MA (US)

(72) Inventor: Alexander J. Camacho, Natick, MA (US)

(*) Notice: Subject to any disclaimer, the term of this patent is extended or adjusted under 35 U.S.C. 154(b) by 763 days.

(21) Appl. No.: 15/004,941

(22) Filed: Jan. 23, 2016

(65) Prior Publication Data
US 2016/0213546 A1    Jul. 28, 2016

Related U.S. Application Data

(60) Provisional application No. 62/107,393, filed on Jan. 24, 2015.

(51) Int. Cl.
*A61F 5/00* (2006.01)
*A61F 5/34* (2006.01)
*A61F 13/00* (2006.01)

(52) U.S. Cl.
CPC .......... *A61F 5/34* (2013.01); *A61F 13/00068* (2013.01)

(58) Field of Classification Search
CPC ............... A61F 5/34; A61F 13/000068; A61F 13/00068
See application file for complete search history.

(56) References Cited

U.S. PATENT DOCUMENTS

| | | | | |
|---|---|---|---|---|
| 5,109,837 A | * | 5/1992 | Gamow | A61G 10/026 128/200.24 |
| 5,865,722 A | * | 2/1999 | Heng | A61M 35/00 600/21 |
| 5,984,351 A | * | 11/1999 | Pierotti | B60R 21/268 102/531 |
| 9,713,570 B2 | * | 7/2017 | Torok | A61M 35/00 |
| 2005/0254993 A1 | * | 11/2005 | Tanaka | A61H 35/00 422/33 |
| 2005/0261615 A1 | * | 11/2005 | Weston | A61M 1/008 602/13 |
| 2006/0100556 A1 | * | 5/2006 | Hargens | A61H 9/005 601/11 |
| 2006/0261579 A1 | * | 11/2006 | Breed | B60R 21/205 280/729 |
| 2016/0256638 A1 | * | 9/2016 | Sarangapani | A61F 13/00063 |

* cited by examiner

*Primary Examiner* — Steven O Douglas

(57) ABSTRACT

Pressurized wound treatment devices and methods of use are provided herein. In some embodiments, such devices provide consistent or adjustable pressure to a treatment site. Such devices and methods are useful, for example, in treating or preventing inflammation and/or blood flow or loss at a treatment site.

15 Claims, 2 Drawing Sheets

PRESSURIZED TREATMENT DEVICES AND METHODS OF USE THEREOF

CROSS-REFERENCE TO RELATED APPLICATION

This application claims priority to and the benefit of U.S. Provisional Application No. 62/107,393, filed on Jan. 24, 2015, the entirety of which is incorporated by reference herein.

FIELD OF THE INVENTION

Embodiments of the present invention generally relate to wound treatment devices, and more particularly to pressurized wound treatment devices to control inflammation and/or blood flow or loss at a wound site.

BACKGROUND OF THE INVENTION

Traditional devices and methods for the treatment of an open, bleeding, or inflamed wound or injury involve wound dressings, cold compresses, bandage wraps, and the like. These devices are used with manual pressure to stave off blood loss or excessive inflammation and are typically most effective when applied immediately following injury. However, such devices require the injured individual or another party to apply or administer the pressure required to treat the wound or inflammation. In urgent or emergency situations, it may not be practical or even possible to deliver the required treatment when needed or for the required duration. Furthermore, such devices are seldom useful to treat a wound covering significant surface area or an area comprising multiple, scattered or diffused wound sites, such as may be seen on a battlefield. Accordingly, a need remains for improved wound treatment devices.

SUMMARY OF THE INVENTION

The invention disclosed herein is directed to pressurized wound treatment devices for use in new or open wounds or other conditions (including, for example, auto-inflammatory diseases or syndromes, or blood disorders such as hemophilia) or open or closed injuries (including, for example, hematomas, fractures, soft tissue sprains, muscle strains, etc.) that may be expected to result in bleeding, inflammation, swelling, contusions, or irritation, or that may be subject to infection. The invention also provides wound therapy devices for the use in connection with chronic or non-healing wounds or conditions that may be treated with pressure. Aspects of the invention further provide for devices and methods for quickly sealing or closing a wound or multiple wounds, either concurrently or serially or both.

In one embodiment, the invention provides a device for applying pressure to a treatment site on a user, the device comprising a reservoir, container or tank having an inlet for addition of a fluid to the interior of the reservoir, container or tank, an entrance for receipt of a body part on which the treatment site is located, optionally a port for addition of a gas, and optionally a pressure gauge configured to register the pressure in the interior of the reservoir, container or tank.

In another embodiment, the device may comprise an inflatable balloon or other expandable or partially expandable reservoir configured to wrap around the body part on which the treatment site is located, such that, when inflated, the reservoir or balloon forms an entrance and a receptacle for receipt of the body part; and a self-inflating mechanism; and optionally a pressure gauge configured to register the pressure in the receptacle.

According to yet another embodiment, the invention provides methods for treating or preventing inflammation and/or bleeding at a treatment site of a user. In one aspect, the method comprises applying a device according to the invention to a treatment site, and pressurizing the device to a pressure suitable for treating or preventing inflammation and/or bleeding at the treatment site.

In certain embodiments, devices according to the invention may use fluid or gas pressure, or a combination of fluid and gas pressure, applied directly to the wound site. In some embodiments, fluids useful in the invention may include water, saline solutions, nutrient solutions, therapeutic or pharmaceutical solutions (such as, for example, a solution containing an antibiotic, antimicrobial, and/or antifungal agent, or a solution containing an agent to expedite a wound healing or sealing, or new tissue growth), cell suspensions (such as, for example, epithelial or endothelial cell compositions in an aqueous solution), blood or blood derivative solutions, hydrogel solutions, oil compounds, combination solutions, other fluids, or any combination of the foregoing. In some embodiments, such devices may use fluid pressure applied indirectly or partially indirectly to the wound site through a dressing, membrane, silicone, hydrogel, matrix, mesh, graft, other components, or any combination of the foregoing.

In some embodiments, devices of the invention comprise a volume of fluid, such as water, in a tank or other container. The tank may be sized and shaped to allow the submersion of a wounded body part such as a limb or digit, and to contain a volume of fluid sufficient to provide the required amount of pressure to control blood flow or inflammation at the wound site. Aspects of the invention also provide for a full body tank or reservoir, which may be useful in the treatment of massive or multiple wound sites, or for some forms of internal bleeding. Such full body reservoirs may allow for the head to remain above the fluid line or may allow complete submersion when outfitted with an oxygen source and delivery line to the patient. In another embodiment, a tank in the shape of an open cylinder may be used. The open cylinder may surround or encompass a wounded body part prior to being pressurized with a fluid. For example, a cylinder tank may be used on a wounded forearm with the elbow emerging on one end and the hand emerging on the other end. Each end of the cylinder may be sealed with, for example, silicone grips that seal against the skin of the forearm. The cylinder may then be filled to stop bleeding and reduce inflammation. Aspects of the invention also provide that the fluid and/or gas may be chilled or heated for therapeutic benefit depending on the nature of the injury. Other aspects of the invention provide for actively pressurized fluid. In one embodiment, pressurized air or gas may be injected into a fluid-containing device to increase the internal pressure. In another embodiment, the device may be pressurized by decreasing the internal capacity or volume of the device. For example, a device may be constructed or lined with a material, such as an inert elastic or compliant material, that can tightened, constrained, or constricted.

According to another embodiment, devices according to the present invention may employ air or gas as the sole or primary mechanism for pressurizing the device. In one embodiment, the device may include an inflatable sleeve or an inflatable component applied with or integrated into wound dressing or wrap. Such device may be inflated before or after application to the treatment site. In some embodiment, the device is self-pressurizing. In a preferred embodiment, the device is adjustable such that the sleeve or wound dressing/wrap may be applied to the treatment site, and then inflated to increase the pressure as desired, either locally at the wound site or throughout the entire device. In a pre-inflated state, such devices may be compact, lightweight, transportable, and easily stowed. In use, such devices may allow consistent or adjustable pressure to be delivered hands-free to the wound site, allowing the injured party to be otherwise mobile with full use of uninjured body parts.

Devices according to the invention may be modular and/or may comprise modular, compact, compressible, expandable, or collapsible components or features. According to certain embodiments of the invention, such devices may be stored in a completely or partially disassembled state for easier storage or transport, or for customization on need. Further, some or all aspects of devices according to the invention may be disposable, reusable, fixed, interchangeable, replaceable, uniform, and/or customized. The invention further contemplates that such devices may include sterile or sanitized components or features.

DETAILED DESCRIPTION

Figure 1:
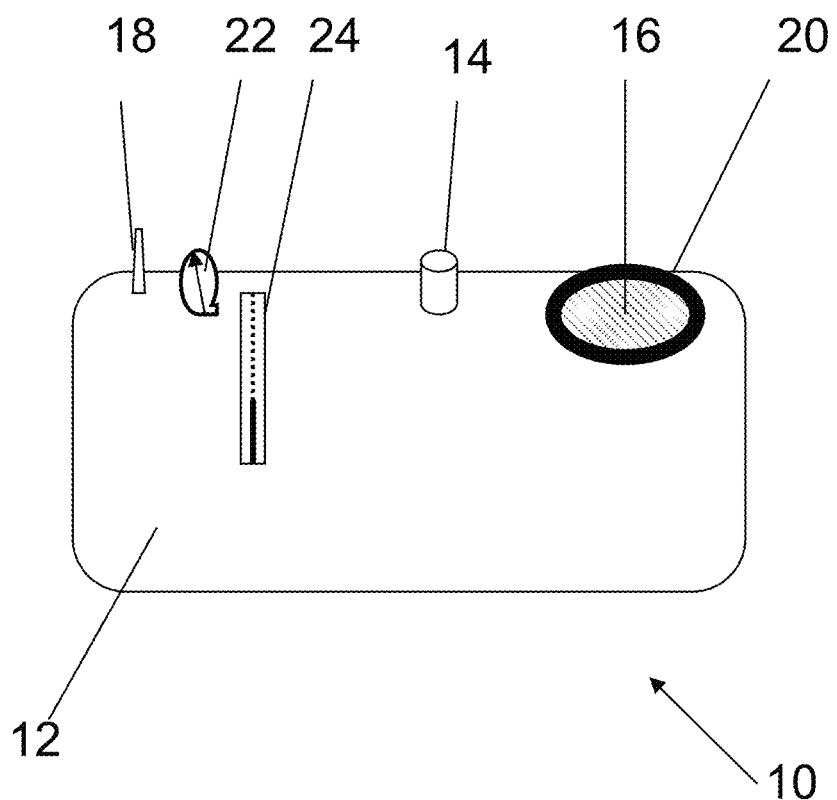
FIG. 1 depicts an embodiment of the invention comprising a tank of liquid to apply pressure directly to a wound or treatment site.

The invention provides devices and methods for administering pressure to a wound site. Devices according to the invention may be used to treat bleeding or inflammation-inducing conditions or injuries and may rely, in whole or in part, on fluid and/or gas pressure. Fluids and/or gases useful in the invention may comprise therapeutic agents or have therapeutic effects when pressurized and directly administered to the treatment site. Accordingly, devices and methods of the invention are also useful to treat chronic or non-healing wounds such as ulcerated or infected wounds. Alternatively or in addition, devices according to the invention may also be used to treat a burn, abrasion, skin graft site, psoriasis plaques, scales, infections or inflictions of the skin or nails (such as a bacterial, fungal or parasitic infection), or as a rejuvenating, beautifying, or other non-medical or cosmetic treatment. In such alternative or additional cases, the devices may be used to administer the desired treatment but not necessarily to treat inflammation and/or blood flow or loss.

Fluids and gases useful in the invention may include, without limitation, compressible fluids and gases. Fluids useful in the invention may comprise, for example, water, saline solutions, nutrient solutions, therapeutic or pharmaceutical solutions, antibiotic or antimicrobial solutions, cell suspensions (such as, for example, epithelial or endothelial cell compositions in an aqueous solution), blood or blood derivative solutions, hydrogel solutions, oil compounds, combination solutions, other fluids, or any combination of the foregoing. Gases useful in the invention comprise, for example, ambient air, carbon dioxide, oxygen, nitrogen, nitrogen dioxide, and inert gases such as noble gases. Therapeutic agents useful in the invention include, for example, antiseptic agents, antibacterial agents, antimicrobial agents, antiviral agents, antifungal agents, antiparasitic agents, iodine, hydrogen peroxide, silver, silver complexes, hydrogen peroxide, acetic acid, sodium hypochlorite, silver nitrate, chlorhexidine gluconate, glycerin, glycol, propylene glycol, polyethylene glycol, ethyl alcohol, isopropyl alcohol, honey, antiaging agents, regenerating agents, soothing agents, or any combination of the foregoing.

According to one embodiment of the invention, the device uses fluid pressure applied directly to the wound or treatment site. In other embodiments, such devices may use fluid pressure applied indirectly or partially indirectly to the wound or treatment site through a liner, dressing, membrane, silicone, hydrogel, matrix, mesh, graft, other physical or chemical barrier other components, or any combination of the foregoing. In some embodiments, devices of the invention comprise a volume of fluid, such as water, in a reservoir, tank or other container. The reservoir may be sized and shaped to allow the submersion of a body part such as all or part of a limb or digit, such as an arm, shoulder, elbow, wrist, hand, finger, thumb, leg, hip, thigh, knee, calf, ankle, foot or toe, and to contain a volume of fluid sufficient to provide the required amount of pressure to control blood flow or inflammation at the wound or treatment site or to administer an alternative treatment. According to the invention, the reservoir may be composed of soft, semi-soft, compliant, partially compliant, hard, durable or fixed materials, or any combination of the foregoing, or the reservoir may be assembled from multiple materials or components have different characteristics. Aspects of the invention also provide for a full body reservoir or tank that may be useful, for example, in the treatment of massive or multiple wound sites, or for some forms of internal bleeding. Such full body reservoirs or tanks may allow for the head to remain above the fluid line or may allow complete submersion when outfitted with an oxygen source and delivery line to the patient. In another embodiment, a reservoir or tank in the shape of an open cylinder or a closed capsule may be used. The open cylinder may surround or encompass a wounded body part prior to being pressurized with a fluid. For example, a cylinder reservoir tank may be used on a wounded forearm with the elbow emerging on one end and the hand emerging on the other end. Each end of the cylinder may be sealed with, for example, silicone grips that seal against the skin of the forearm. The cylinder could then be filled to stop bleeding and control inflammation. Aspects of the invention also provide that the fluid may be chilled or heated for therapeutic benefit depending on the nature of the intended treatment.

In some embodiments, aspects of the invention provide for actively pressurized fluid and/or gas. For example, pressurized air or gas may be injected into a fluid-containing device to increase internal pressure. In another embodiment, the fluid and/or gas existing in the device may be compressed to increase internal pressure. According to one embodiment, such devices may be configured with a valved opening, comprising for example a presta-style valve, for blowing air into to device. Such opening may be configured for application of an air pump to the device or for inflating by mouth. In another embodiment, the device may be pressurized by decreasing the internal capacity or volume of the device. For example, a device may be constructed or lined with material, such as an elastic or compliant material, that can tightened, constrained, or constricted. In some embodiments, a device may comprise a manual or power-driven pressurizer to actively pressurize the device. According to one aspect, a power-driven pressurizer comprises a power source, such as battery, and an actuator to apply or increase the pressure within the device. Such a power-driven pressurizer may be a pyrotechnic initiator for setting off a self-inflation reaction within the device. According to another aspect, a device according to the invention may comprise a manual or mechanical component to apply pressure. For example, such a component may comprise a tightening mechanism to constrict the internal capacity of the device.

According to another embodiment, a device of the present invention may employ air or gas as the sole or primary mechanism for pressurizing the device. In one embodiment, the device may include an inflatable sleeve or an inflatable component applied with or integrated into wound dressing or wrap. Such device may be inflated before or after application to the wound site. In some embodiment, the device is self-pressurizing. Embodiments of the invention may employ self-inflating technology, such as that in use with self-inflating life preservers on aircraft or airbags in motor vehicles. In some self-pressuring embodiments, devices of the invention may comprise a propellant component, a pyrotechnic initiator, or both. In a preferred embodiment, the device is adjustable such that the sleeve or wound dressing/wrap may be applied to the wound or treatment site, and then inflated to increase the pressure as desired, either locally at the wound or treatment site or throughout the entire device. In a pre-inflated state, such devices may be compact, lightweight, transportable, and easily stowed. In use, such devices would allow consistent or adjustable pressure to be delivered hands-free to the treatment site, allowing the user to be otherwise mobile with full use of uninjured body parts.

In some embodiments, devices according to the invention may be modular and/or may comprise modular, compact, compressible, expandable, or collapsible components or features. According to certain embodiments of the invention, such devices may be stored in a completely or partially disassembled state for easier storage or transport, or for customization on need. Further, some or all aspects of devices according to the invention may be disposable, reusable, fixed, interchangeable, replaceable, uniform, and/or customized. The invention further contemplates that such devices may include sterile or sanitized components or features.

According to some embodiments, devices of the invention may include a disposable, permanent or replaceable liner or covering that, when the device is in use, is situated on or over the treatment site and functions as a complete or partial barrier between the treatment site and the remainder of the device. According to one embodiment, devices of the invention may be configured to accommodate a separate, potentially optional, treatment site dressing such as a bandage, a hydrogel pad, or gauze padding.

The terms wound, wound site, injury, injury site, treatment site, and variations of the foregoing, are used interchangeably herein in reference to a site of bleeding, inflammation, chronic or non-healing wounds, and/or irritation; or a site at risk of bleeding, inflammation, chronic or non-healing wounds and/or irritation on an individual, or a site otherwise intended for pressurized treatment for any other purpose. Accordingly, any reference to an injured party or wounded party should be understood to include any party experiencing actual bleeding, inflammation, chronic or non-healing wounds, irritation, or any combination of the foregoing; any party who is at risk for bleeding, inflammation, chronic or non-healing wounds, irritation or any combination of the foregoing; and any party who is experiencing actual bleeding, inflammation, chronic or non-healing wounds, irritation or any combination of the foregoing and who is also at risk for increased bleeding, inflammation, chronic or non-healing wounds or any combination of the foregoing; or any party undergoing pressurized treatment for any other purpose. While aspects of the devices and methods of the invention may be described herein in terms of treatment sites on a person or a user, such description should be understood to be non-limiting as the invention is applicable for use on a treatment site of other living entities, including without limitation, animals, mammals, birds, reptiles, amphibians, and fish. In some embodiments, devices and methods of the invention are configured for use with an animal such as, without limitation, a dog, cat, rat, rabbit, pig, cow, goat, sheep, horse, or a pack animal such as a mule.

The following examples are to be considered illustrative and thus are not limiting of the remainder of the disclosure in any way whatsoever.

An example of a non-limiting embodiment of the invention is depicted in FIG. 1. According to this embodiment, the device (10) comprises a water-tight tank (12) comprising an inlet (14) for a water source, an entry opening or entrance (16) for insertion of a hand, foot, arm or leg, and an optional port (18) for a gas line. In some embodiments, a single opening may serve as both the water inlet (14) and the entrance (16). In use, the device (10) is filled partially or completely to capacity with water or saline comprising, optionally, a therapeutic agent, through the inlet (14). In another embodiment, the device may not include an inlet and/or a port but me be already filled with a fluid or gas. The body part where the treatment site is located is then inserted into the device (10) through the entrance (16). The entrance (16) may comprise a seal (20) such as a silicon band or adjustable cuff to seal the device (10) around the body part once the treatment site has been placed in the device. The pressure on the treatment site will be greater than the ambient air pressure due, in part, to the weight of the water. However, if additional pressure is desired, a gas line may be attached to the port (18) and gas may be injected into the device (10) to increase the pressure within the device (10). To measure or monitor the pressure and/or temperature within the device (10), the tank (12) may optionally be outfitted with a pressure gauge (22), a thermometer (24), or both. A device according to the invention, such as the embodiment shown in FIG. 1, may be collapsible and composed of lightweight, durable materials to allow for easy transport and storage. In some embodiments, the device may be disposable or it may be reusable. In the latter embodiment, the device may be constructed of materials suitable for cleaning or sterilization by any means such as autoclaving, radiation, or chemical cleaning. In use, this device allows the application of constant or adjustable pressure to a treatment site without requiring continual action by the user or treatment administrator.

Figure 2:
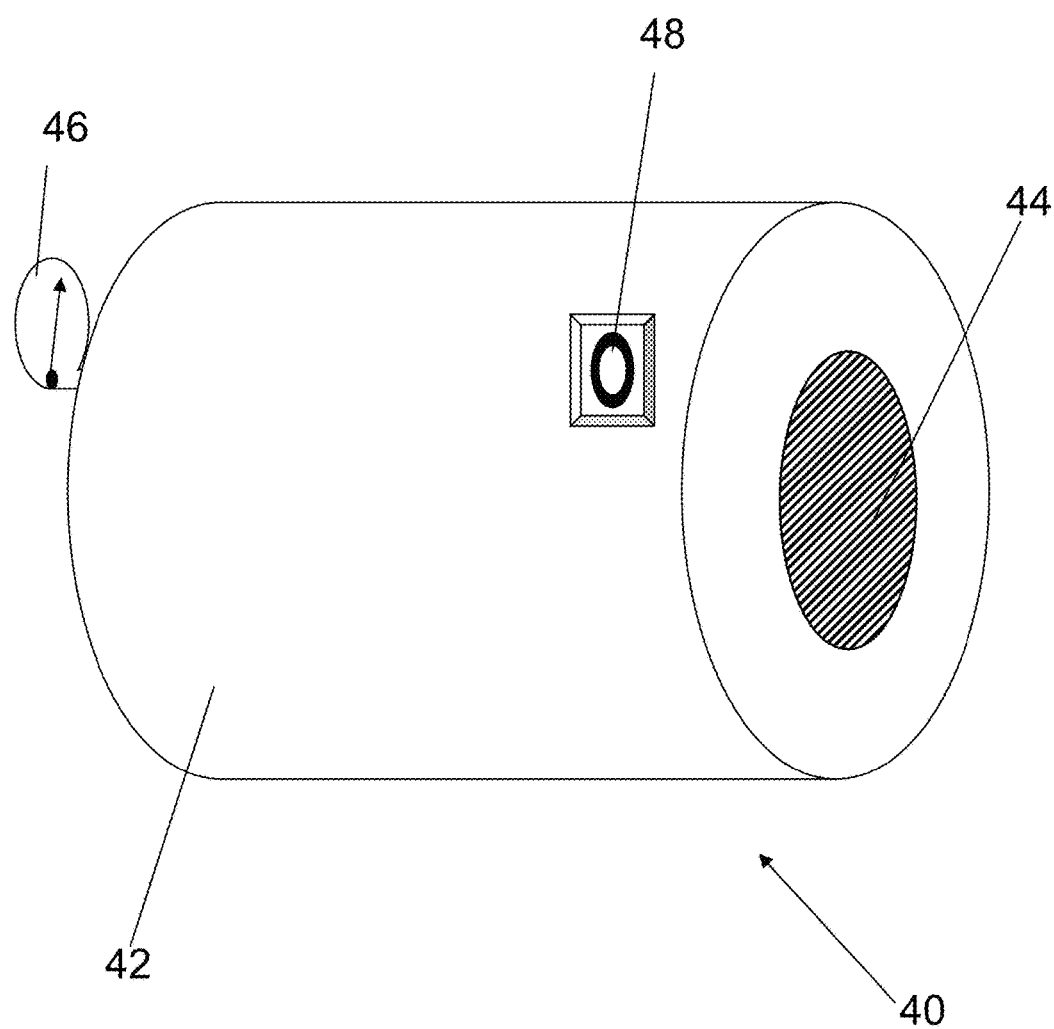
FIG. 2 depicts an embodiment of the invention comprising an inflatable reservoir integrated into a device.

FIG. 2 depicts another non-limiting embodiment of the invention. According to this embodiment, the device (40) comprises an inflatable balloon (42) that is sized and configured as a sleeve to accommodate a forearm of an adult person. The balloon forms a open tube-within-a-tube cylindrical configuration, allowing the user to place his or her forearm in the interior tube passageway as a treatment receptacle (44) and then inflate the device (40), resulting in an inflated cuff wrapping around the user's forearm. Although described in FIG. 2 as passageway, the treatment receptacle (44) may have another configuration, such as a closed receptacle with only an entry opening rather than an open-ended passageway. In this embodiment, the device (40) is self-pressuring by way of the same technology deployed in flotation vests found on passenger aircraft. In a variation of this embodiment, the device (40) may self-inflate with the action of a contained propellant, and an initiator much like standard airbag technology but with designed to effect a sustainable pressure suitable for wound treatment. The pressure may be measured or monitored with an optional pressure gauge (46). In the embodiment shown in FIG. 2, it is contemplated that the device (40) may be single-handedly actuated quickly by way of a switch, button or other actuator (48) to apply a consistent level of pressure, leaving the user with full use of his or her other limbs. In another embodiment, such a device may be pressurized by inflating the balloon by mouth using a port or opening. When not in use, the device according to FIG. 2 may be stored flat, rolled, folded or otherwise packed.

Having disclosed exemplary embodiments of the present invention, it should be noted by those skilled in the art that the disclosures are exemplary only and that various other alternatives, adaptations and modifications may be made within the scope of the present invention. Accordingly, the present invention is not limited to the specific embodiments as illustrated herein. Without further elaboration, it is believed that one skilled in the art can, using the preceding description, utilize the present invention to its fullest extent.

I claim:

1. A device for applying pressure to a treatment site on a user, the device comprising
    an inflatable balloon configured to surround a body part comprising the treatment site, such that, when inflated, the balloon comprises an entrance for receipt of the body part and a pressurized treatment receptacle;
    a self-inflating mechanism comprising a propellant and an initiator; and
    a pressure gauge configured to register the pressure in the treatment receptacle.

2. A method for treating or preventing inflammation or bleeding at a treatment site of a user, the method comprising
    applying the device of claim 1 to the treatment site; and
    pressurizing the treatment receptacle by initiating a self-inflation reaction through the self-inflating mechanism,
thereby to treat or prevent inflammation and/or bleeding at the treatment site.

3. The device of claim 1, wherein the initiator is a pyrotechnic initiator.

4. The device of claim 1, wherein the self-inflating mechanism further comprises an actuator.

5. The device of claim 1, wherein the self-inflating mechanism is a power-driven pressurizer and further comprises a battery.

6. The device of claim 1, wherein the balloon, when inflated, forms a tube-within-a-tube configuration having an interior tube passageway, and wherein such passageway comprises the treatment receptacle.

7. The device of claim 1, wherein the balloon is sized and configured as a sleeve.

8. A device for treating or preventing inflammation or bleeding at a treatment site of a user, the device comprising
    an expandable or partially expandable reservoir which, when expanded, forms an entrance for receipt of a body part on which a treatment site is located, and a pressurized treatment receptacle; and
    a pressurizing mechanism comprising a propellant and an initiator.

9. The device of claim 8, wherein the initiator is a pyrotechnic initiator.

10. The device of claim 8, wherein the pressurizing mechanism further comprises an actuator.

11. The device of claim 8, wherein the pressuring mechanism is a power-driven pressurizer and further comprises a battery.

12. The device of claim 8, wherein the reservoir, when expanded, forms a tube-within-a-tube configuration having an interior tube passageway, and wherein such passageway comprises the treatment receptacle.

13. The device of claim 8, wherein the reservoir is sized and configured as a sleeve.

14. A method for treating or preventing inflammation or bleeding at a treatment site of a user, the method comprising
    applying the device of claim 8 to the treatment site; and
    pressurizing the treatment receptacle by initiating a self-inflation reaction through the pressurizing mechanism,
thereby to treat or prevent inflammation and/or bleeding at the treatment site.

15. A device for treating or preventing inflammation or bleeding at a treatment site of a user, the device comprising
    an expandable or partially expandable reservoir which, when expanded, forms an entrance for receipt of a body part on which a treatment site is located, and a pressurized treatment receptacle; and
    a pressurizing mechanism comprising a propellant, a pyrotechnic initiator, a battery power source, and an actuator,
    wherein the reservoir, when expanded, forms a tube-within-a-tube configuration having an interior tube passageway, and wherein such passageway comprises the treatment receptacle.

* * * * *